United States Patent
Mintchev et al.

(10) Patent No.: US 8,852,083 B2
(45) Date of Patent: Oct. 7, 2014

(54) SELF-STABILIZED ENCAPSULATED IMAGING SYSTEM

(75) Inventors: Martin P. Mintchev, Calgary (CA); Orly Yadid-Pecht, Haifa (IL)

(73) Assignee: UTI Limited Partnership, Calgary, Alberta (CA)

( * ) Notice: Subject to any disclaimer, the term of this patent is extended or adjusted under 35 U.S.C. 154(b) by 1235 days.

(21) Appl. No.: 11/347,862

(22) Filed: Feb. 6, 2006

(65) Prior Publication Data

US 2006/0178557 A1 Aug. 10, 2006

Related U.S. Application Data

(60) Provisional application No. 60/650,278, filed on Feb. 4, 2005.

(51) Int. Cl.
*A61B 1/00* (2006.01)

(52) U.S. Cl.
USPC .......................................... 600/117; 600/116

(58) Field of Classification Search
USPC ......... 600/101, 104, 109, 115–118, 121, 160, 600/178, 476, 103; 604/99.01, 101.01, 103, 604/103.03, 103.05
See application file for complete search history.

(56) References Cited

U.S. PATENT DOCUMENTS

| | | | |
|---|---|---|---|
| 4,217,045 A * | 8/1980 | Ziskind | 396/17 |
| 4,632,119 A | 12/1986 | Reichstein | |
| 4,748,562 A | 5/1988 | Miller | |
| 4,981,470 A | 1/1991 | Bombeck | |
| 5,109,870 A | 5/1992 | Silny | |
| 5,152,277 A * | 10/1992 | Honda et al. | 600/116 |
| 5,234,457 A * | 8/1993 | Andersen | 606/198 |

(Continued)

FOREIGN PATENT DOCUMENTS

WO 2004041068 5/2004

OTHER PUBLICATIONS

Mintchev, M.P., U.S. Appl. No. 60/664,633, filed Mar. 24, 2005.

(Continued)

*Primary Examiner* — Anhtuan T Nguyen
*Assistant Examiner* — Rynae Boler
(74) *Attorney, Agent, or Firm* — Fulbright & Jaworski LLP (57) ABSTRACT

Wireless capsule endoscope technology has been used to image portions of the gastrointestinal (GI) tract, particularly the small bowel. However in other GI organs, especially those having larger-lumens, the capsule may become destabilized and tumble, precluding meaningful interpretation of the acquired images. The present invention describes a method and apparatus for permitting capsule imaging of organs having larger-lumens without tumbling, and includes an outer shell surrounding the capsule that targets the colon, as an example. Once the colon has been reached, the shell breaks or dissolves, and allows expansion of expandable materials attached to each end of the capsule, thereby stabilizing the capsule in the targeted organ, while permitting it to be moved by peristalsis and/or other means for locating the capsule. Imagers and light emitting diodes (LEDs) are activated during the expansion process, and enable overlapping of images. The capsule is moved through the colon, taking images at chosen frame rates with data being wirelessly transmitted by means of an RF transmitter, and is eventually expelled from the body.

22 Claims, 5 Drawing Sheets

(56) References Cited

U.S. PATENT DOCUMENTS

| | | | |
|---|---|---|---|
| 5,297,437 | A | 3/1994 | Schneider |
| 5,320,605 | A * | 6/1994 | Sahota ............... 604/101.01 |
| 5,411,477 | A | 5/1995 | Saab |
| 5,438,985 | A | 8/1995 | Essen-Moller |
| 5,604,531 | A | 2/1997 | Iddan |
| 5,681,260 | A | 10/1997 | Ueda |
| 5,688,776 | A | 11/1997 | Bauer |
| 5,792,048 | A | 8/1998 | Schaefer |
| 5,800,341 | A * | 9/1998 | McKenna et al. ............ 600/109 |
| 5,833,625 | A | 11/1998 | Essen-Moller |
| 5,857,998 | A * | 1/1999 | Barry ............... 604/103.03 |
| 6,153,222 | A | 11/2000 | Becher |
| 6,285,897 | B1 | 9/2001 | Kilcoyne |
| 6,374,670 | B1 | 4/2002 | Spelman |
| 6,475,145 | B1 | 11/2002 | Baylor |
| 6,505,654 | B1 | 1/2003 | Andersen |
| 6,635,834 | B1 | 10/2003 | Wenner |
| 6,689,056 | B1 | 2/2004 | Kilcoyne |
| 6,776,165 | B2 | 8/2004 | Jin |
| 6,799,462 | B1 | 10/2004 | Berstis |
| 7,061,523 | B2 | 6/2006 | Fujita |
| 7,104,952 | B2 | 9/2006 | Iddan |
| 7,142,908 | B2 | 11/2006 | Glukhovsky |
| 7,160,258 | B2 * | 1/2007 | Imran et al. ............ 600/593 |
| 7,192,397 | B2 * | 3/2007 | Lewkowicz et al. .......... 600/160 |
| 2002/0109774 | A1 * | 8/2002 | Meron et al. ............ 348/74 |
| 2002/0187721 | A1 | 12/2002 | Chung |
| 2002/0198470 | A1 * | 12/2002 | Imran et al. ............ 600/587 |
| 2003/0018280 | A1 * | 1/2003 | Lewkowicz et al. .......... 600/549 |
| 2003/0020810 | A1 | 1/2003 | Takizawa |
| 2003/0085994 | A1 * | 5/2003 | Fujita et al. ............ 348/77 |
| 2003/0125788 | A1 | 7/2003 | Long |
| 2003/0216622 | A1 * | 11/2003 | Meron et al. ............ 600/300 |
| 2004/0015150 | A1 * | 1/2004 | Zadno-Azizi ............ 604/523 |
| 2004/0068204 | A1 * | 4/2004 | Imran et al. ............ 600/593 |
| 2004/0162469 | A1 * | 8/2004 | Imran ............ 600/310 |
| 2004/0192582 | A1 | 9/2004 | Burnett |
| 2004/0199054 | A1 | 10/2004 | Wakefield |
| 2004/0225190 | A1 * | 11/2004 | Kimoto et al. ............ 600/177 |
| 2004/0253304 | A1 * | 12/2004 | Gross et al. ............ 424/451 |
| 2005/0043634 | A1 | 2/2005 | Yokoi |
| 2005/0054902 | A1 | 3/2005 | Konno |
| 2005/0124875 | A1 * | 6/2005 | Kawano et al. ............ 600/407 |
| 2005/0183733 | A1 * | 8/2005 | Kawano et al. ............ 128/899 |
| 2005/0186244 | A1 | 8/2005 | Hunter |
| 2005/0187140 | A1 | 8/2005 | Hunter |
| 2005/0196421 | A1 | 9/2005 | Hunter |
| 2005/0208095 | A1 | 9/2005 | Hunter |
| 2005/0216231 | A1 | 9/2005 | Aoki |
| 2005/0250991 | A1 | 11/2005 | Mizuno |
| 2005/0256372 | A1 | 11/2005 | Yokoi |
| 2005/0266074 | A1 | 12/2005 | Zilberstein |
| 2005/0272973 | A1 | 12/2005 | Kawano |
| 2005/0288557 | A1 | 12/2005 | Yokoi |
| 2006/0004255 | A1 * | 1/2006 | Iddan et al. ............ 600/160 |
| 2006/0030752 | A1 | 2/2006 | Orihara |
| 2006/0063974 | A1 | 3/2006 | Uchiyama |
| 2006/0116564 | A1 | 6/2006 | Mintchev |
| 2006/0152309 | A1 | 7/2006 | Mintchev |
| 2006/0162452 | A1 | 7/2006 | Moser |
| 2006/0169294 | A1 | 8/2006 | Kaler |
| 2006/0178557 | A1 | 8/2006 | Mintchev |
| 2006/0209185 | A1 | 9/2006 | Yokoi |
| 2006/0229592 | A1 | 10/2006 | Yokoi |
| 2006/0231110 | A1 | 10/2006 | Mintchev |
| 2006/0238614 | A1 | 10/2006 | Konno |
| 2006/0252986 | A1 | 11/2006 | Akagi |
| 2006/0258901 | A1 | 11/2006 | Fujimori |
| 2006/0264083 | A1 | 11/2006 | Fujimori |
| 2006/0264704 | A1 | 11/2006 | Fujimori |
| 2006/0264709 | A1 | 11/2006 | Fujimori |
| 2007/0010702 | A1 | 1/2007 | Wang |
| 2007/0030344 | A1 | 2/2007 | Miyamoto |
| 2007/0032698 | A1 | 2/2007 | Uchimura |
| 2007/0032699 | A1 | 2/2007 | Segawa |

OTHER PUBLICATIONS

Morgan, P.N., et al, "Resistive Homogeneous MRI Magnet Design by Matrix Subset Selection," Magnetic Resonance in Medicine, Jun. 1999, pp. 1221-1229, vol. 41.

Nelson, C., et al., "National Ambulatory Medical Care Survey: 1993 summary," [abst] Vital Health Stat. 13, Apr. 1998, pp. 1-99.

Olympus Inc., "Development of Capsule . . . ," Nov. 30, 2004, <http://www.olympus-global.com/en/news/2004b/nr041130capsle.cfm?ote=1&nr=1> [retrieved Jan. 17, 2007].

Pandolfino, J.E., et al., "AGA Technical Review on the Clinical Use of Esophageal Manometry," Gastroenterology, Jan. 2005, pp. 209-224, vol. 128.

Pandolfino, J.E., et al., "Ambulatory Esophageal pH Monitoring Using . . . etc.," The American Journal of Gastroenterology, Apr. 2003, pp. 740-749, vol. 98, Chicago, USA.

Pandolfino, J.E., et al, "American Gastroenterological Association Medical Position Statement . . . etc.," Gastroenterology, Jan. 2005, pp. 207-208, vol. 128.

Pozar, D.M., "Microstrip Antennas," Proceedings of the IEEE, Jan. 1992, pp. 79-91, vol. 80.

"Radiography—Upper GI Tract," Radiological Society of North America, May 2003, <http://www.radiologyinfo.org>, Chicago, USA.

Ren, J., et al., "Determinants of Intrabolus Pressure . . . etc.," Am. J. Physiol. Gastrointest. Liver Phys., Mar. 1993, pp. 407-413, vol. 264, American Physiological Society, USA.

Rhee, E.J., et al., "The Position Control of a Capsule . . . etc.," Journal of Magnetism and Magnetic Materials, Nov. 2002, pp. 350-352, vol. 252.

Ruan, C., et al., "A Wireless pH Sensor Based on the Use of Salt . . . etc.," Sensors and Actuators B: Chemical, Nov. 2003, pp. 61-69, vol. 96.

Sadiku, M., et al., "Magnetic Levitation," IEEE Potentials, Mar. 2006, pp. 41-42, vol. 25(2).

Sendoh, M., et al., "Fabrication of Magnetic . . . etc.," IEEE Trans. on Magnetics, Sep. 2003, pp. 3232-3234, vol. 39(5).

Shaheen, N., et al., "Gastroesophageal Reflux, Barrett Esophagus, and Esophageal . . . etc.," J. Am. Med. Assoc., Apr. 2002, pp. 1972-1981, vol. 287.

Simon, M.D., et al., "Diamagnetically Stablized Magnet Levitation," Amer. Journ. of Phys., Jun. 2001, pp. 702-713, vol. 69(6).

Smout, A.J., "Manometry of the Gastrointestinal Tract: Toy or Tool?" Scandinavian Journal of Gastroenterology Suppl, Nov. 2001, pp. 22-28, vol. 36.

Spiess, A.E., et al., "Treating Achalasia: From Whalebone to Laparoscope," J. Am. Med. Assoc., Aug. 1998, pp. 638-642, vol. 280.

Srinivasan, R., et al., "Esophageal Function Testing Using Multichannel . . . etc.," Amer. Journ. Physiol.: Gastro. and Liver Phys., Mar. 2001, pp. G457-G462, vol. 280.

Fischer, D., et al., "Capsule Endoscopy: The Localization System," [abst], Gastrointestinal Endoscopy Clinics of North America, Jan. 2004, pp. 25-31, vol. 14.

Gavriel, J., et al., "History and Development of Capsule . . . etc.," Gastrointestinal Endoscopy Clinics of North America, Jan. 2004, pp. 1-9, vol. 14.

Geim, A.K., et al., "Diamagnetic Levitation . . . etc.," Journal of Applied Physics, May 2000, pp. 6200-6204, vol. 87(9).

Geim, A.K., et al., "Magnetic Levitation at Your Fingertips," Nature, Jul. 22, 1999, pp. 323-324, vol. 400.

Geim, A.K., et al., "Of Flying Frogs and Levitrons," European Journal of Physics, Jul. 1997, pp. 307-313, vol. 18(4).

Gerson, L.B., et al., "Patient-Derived Health State Utilities . . . etc.," American Journal of Gastroenterology, Mar. 2005, pp. 524-533, vol. 100.

Glukhovsky, A., "Wireless Capsule Endoscopy," Sensor Review, 2003, pp. 128-133, vol. 23(2).

Gonzalez, J.L., et al., "Friction-Assisted Magnetic Holding . . . etc.," Proc. of the 28th IEEE EMBS Annual Int'l Conf., Aug. 30-Sep. 3, 2006, pp. 5944-5947, New York, USA.

(56) References Cited

OTHER PUBLICATIONS

Gonzalez, J.L., et al., "Integrated Esophageal Pressure, pH and Bolus Transit Sensor," Proc. IEEE Sensors, Oct. 2004, pp. 1369-1372, vol. 3, Vienna, Austria.
Goyal, R.K., et al., "Pressure Inversion Point at the Upper High Pressure Zone and its Genesis," Gastroenterology, Apr. 1970, pp. 754-459, vol. 59.
"Hall Effect Sensing and Application", Honeywell, Inc., <http://content.honeywell.com/sensing/prodinfo/solidstate/technical/hallbook.pdf>, [retrieved Jan. 11, 2007].
Holloway, R.N., et al., "Electrical Control Activity of the Lower Esophageal . . . etc.," Am. J. Physiol. Gastroint. Liver Physiol., Apr. 1987, pp. G511-G521, vol. 252.
Hu, C., et al., "Efficient Linear Algorithm . . . etc.," IEEE EMBS 27th Annual International Conference, Sep. 2005, pp. 7143-7146, Shanghai, China.
Hu, C., et al., "Efficient Magnetic Localization . . . etc.," IEEE/RSJ Int'l Intelligent Robots and Systems Conference, Aug. 2005, pp. 628-633, Edmonton, Canada.
Hu, C., PhD Thesis, University of Alberta, Spring 2006, Edmonton, Alberta.
Johnson, L.F., et al., "Development of the 24-Hour Intraesophageal pH Monitoring Composite Scoring System," Journal of Clin. Gastroenterology, 1986, pp. 52-58, vol. 8, USA.
Jui, Y.T., et al., "The ESO-Pill: A Non-Invasive MEMS Capsule . . . etc.," Proc. 2004 11th IEEE Int'l Conf. Elect. Circ. and Syst., Dec. 2004, pp. 427-430, Tel Aviv, Israel.
Kahrilas, P., et al., "American Gastroenterological Association Technical Review on the Clinical . . . etc.," Gastroenterology, Dec. 1994, 1865-1884, vol. 107, Chicago.
Kahrilas, P., et al., "Clinical Esophageal pH Recording: A Technical Review for Practice . . . etc.," Gastroenterology, Jun. 1996, pp. 1981-1996, vol. 110, Illinois, USA.
Kallay, N., et al., "Inner Layer Capacitor at the Solid/Liquid Interface," Croatica Chemica Acta, May 26, 2003, pp. 243-249, vol. 77, Croatia.
Kern, M.K., "Kinematic and Dynamic Characteristics of Solid . . . etc." [abst], Annals of Otol., Rhinol. and Laryngol., Sep. 1996, pp. 716-723, vol. 105, Annals Pub. Co., USA.
Ku, D.N., et al., "A Kinematic Study of the Oropharyngeal Swallowing . . . etc.", Annals of Biomedical Engineering, Nov. 1990, pp. 655-669, vol. 18, No. 6, Springer, Netherlands.
Kubler, C., "Endoscopic Robots," Lecture Notes in Computer Science, Feb. 2000, pp. 949-955, vol. 1935.
Kwan, K.Y., et al., "High-Pressure Balloon Catheter . . . etc." [abst], 9th Int'l Conf on Electronics, Circuits and Systems, Sep. 2002, pp. 1211-1214, vol. 3, Dubrovnik, Croatia.
Lauto, A., et al, "Self-Expandable Chitosan Stent: Design and Preparation," Biomaterials, Jul. 2001, pp. 1869-1874, vol. 22.
Layne, K.A., et al., "Using the Fleming Index of Dysphagia to Establish Prevalence," Dysphagia, Mar. 1989, pp. 39-42, vol. 4(1).
Lee, W.F., et al., "Electrical Modeling of MEMS Sensor for Integrated Accelerometer Applications," Electron Devices Meeting, Jun. 1999, pp. 88-91, IEEE Hong Kong, Hong Kong.
Lewis, B.S., "The Utility of Capsule Endoscopy in Obscure Gastrointestinal Bleeding," Techniques in Gastrointestinal Endoscopy, Jul. 2003, pp. 115-120, vol. 5(3).
Lindgren, S., et al., "Prevalence of Swallowing Complaints and Clinical Findings Among . . . etc.," Dysphagia, Dec. 1991, pp. 187-189, vol. 6(4).
Locke, G.R, et al., "Prevalence and Clinical Spectrum of Gastroesophageal Reflux . . . etc.," Gastroenterology, May 1997, pp. 1448-1456, vol. 112.
Lynch, J.P., et al., "Design of a Piezoresistive MEMS-Based Accelerometer . . . etc.," Journal of Aerospace Engineering, Jul. 2003, pp. 108-114, vol. 6, Issue 3, ASCE, USA.
Marsden, G., "Levitation! Float Objects in a . . . ," Sep. 2003, <http://www.arttec.net/Press/N&V/Levitation.pdf> [retrieved Jan. 17, 2007].

Menciassi, A., et al., "Shape Memory Alloy Clamping . . . etc.," Journal of Micromechanics and Microengineering, Nov. 2005, pp. 2045-2055, vol. 15(11).
Meng, M., et al., "Wireless Robotic Capsule Endoscopy . . . etc.," IEEE Intelligent Control and Automation 5th World Congress, Jun. 2004, pp. 5561-5565, Hangzhou, China.
Mintchev, M.P., U.S. Appl. No. 60/618,955, filed Oct. 14, 2004.
Mintchev, M.P., U.S. Appl. No. 60/636,474, filed Dec. 15, 2004.
Mintchev, M.P., U.S. Appl. No. 60/643,392, filed Jan. 11, 2005.
Mintchev, M.P., U.S. Appl. No. 60/650,278, filed Feb. 4, 2005.
Abell, T.L., et al., "Glucagon-Evoked Gastric Dysrhythmias I . . . etc.," [abst] Gastroenterology, Jun. 1985, pp. 1932-1940, vol. 88.
Al-Zaben, A., et al., "Analysis of Intraluminal Impedance Measurements," Physiological Measurements, Nov. 2003, pp. 837-845, vol. 24.
Al-Zaben, A., et al., "Computation of Intraluminal Impedance," Physiological Measurements, Feb. 2004, pp. 61-70, vol. 25, England.
Asher, G.M., et al., "An Equivalent Circuit Approach . . . etc.," IEEE Transaction on Magnetics, Mar. 1982, pp. 692-697, vol. 18(2).
Barie, W., et al., "Linear and Nonlinear State-Space . . . etc.," Int'l Journal of Systems Science, Nov. 1996, pp. 1153-1163, vol. 27(11).
Baschirotto, A., et al., "A Fluxgate Magnetic Sensor . . . etc.," IEEE Transactions on Instrumentation and Measurement, Feb. 2007, pp. 25-31, vol. 56(1).
Bredenoord, A.J., et al., "Minimum Sample Frequency for Multichannel Intraluminal . . . ," Neurogastroenterology and Motility, Dec. 2004, pp. 713-719, vol. 16, The Netherlands.
Bredenoord, A.J., et al., "Reproducibility of Multichannel Intraluminal Electrical . . . etc.," American Journal of Gastroenterology, Feb. 2005, pp. 265-269, vol. 100.
Brin, M.F., and D. Younger, "Neurologic Disorders and Aspiration," Otolaryngol Clin North Am, Nov. 1988, pp. 691-699, vol. 21.
Brondsted, H., et al., "Cross-Linked Dextran—A New Capsule Material for Colon Targeting of Drugs," Journal of Controlled Release, Apr. 30, 1998, pp. 7-13, vol. 53.
Cave, D.R., "Reading Wireless Video Capsule Endoscopy," Gastrointest Endosc Clin N Am, Jan. 2004, pp. 17-24, vol. 14.
Chiba, A., et al., "Magnetic Actuator for Capsule . . . etc.," IEEE Int'l Magnetic Conference, Apr. 2005, pp. 1251-1252, Nagoya, Japan (abstract).
Cibula, E., et al., "Miniature Fiber-Optic Pressure Sensor With a Polymer Diaphragm," Applied Optics, May 2005, pp. 2736-2744, vol. 44.
De Franchis, R., "Small Bowel Malignancy," [abst] Gastrointestinal Endoscopy Clinics of North America, Jan. 2004, pp. 139-148, vol. 14.
Donlagic, D., et al., "All-Fiber High-Sensitivity Pressure Sensor With SiO2 Diaphragm," Applied Optics, Aug. 2005, pp. 2071-2073, vol. 30.
Fajardo, N.R., et al. "Esophageal Perforation After Placement of Wireless Bravo pH Probe," Gastrointest Endosc, Jan. 2006, pp. 184-185, vol. 63(1).
Fass, J., et al., "Measuring Esophageal Motility with a New . . . etc." (abstract), Scand. Journal of Gastroenterology, Aug. 1994, pp. 693-702, vol. 29, Norway.
Fass, R., et al., "Effect of ambulatory 24-hour esophageal pH monitoring on reflux-provoking . . . etc.", Digestive Diseases and Sciences, Nov. 1999, pp. 2263-2269, vol. 44.
Stein, H.J., et al., "'Efficacy' of Esophageal Peristalsis: A Manometric Parameter . . . etc.," Diseases of the Esophagus, Dec. 2004, pp. 297-303, vol. 17.
Stendal, C., "Practical Guide to Gastrointestinal Function Testing," Stockholm: Blackwell Science Ltd., 1997.
Thompson, H., et al., "Eddy Current Magnetic Levitation . . . etc.," IEEE Potentials, Feb. 2000, pp. 42-44, vol. 19(1).
Tibbling, L., et al., "Dysphagia and its Consequences in the Elderly," Dysphagia, Dec. 1991, pp. 200-202, vol. 6(4).
Tutuian, R., et al., "Multichannel Intraluminal Impedance in Esophageal Function . . . ," Journal of Clinical Gastroenterology, Sep. 2003, pp. 206-215, vol. 3, Charleston, USA.
Wang, W., "A Study on RF Based . . . etc.," IEEE Mechatronics and Automation 2006 International Conference, Jun. 2006, pp. 1663-1667, Luoyang, China.

(56) References Cited

OTHER PUBLICATIONS

Wang, X., "Physiological Factors of the Small . . . etc.," IEEE EMBS 27th Annual International Conference, Sep. 2005, pp. 2942-2945, Shanghai, China.

Weusten, B.L.A.M., et al., "Spatiotemporal Characteristics of Physiological Gastroesophageal Reflux," Mar. 1994, American Journal of Physiology, pp. G357-G362, vol. 266, USA.

Wikipedia, the Free Encyclopedia, "Magnetic Levitation," Jun. 21, 2005, <http://en.wikipedia.org/wiki/magnetic_levitation> [retrieved Jan. 11, 2007].

Wu, B., U.S. Appl. No. 60/719,887, filed Sep. 23, 2005.

Xie, X., "Micro-System Design . . . etc.," IEEE EMBS 27th Annual International Conference, Sep. 2005, pp. 7135-7138, Shanghai, China.

Yi, J.H., et al., "Robust Force Control for a Magnetically Levitated . . . etc.," Journal for Control Engineering Practice, 1996, pp. 957-965, vol. 4(7).

Zvi, F., et al., "Future of Capsule Endoscopy," Gastrointestinal Endoscopy Clinics of North America, Jan. 2004, pp. 219-227, vol. 14.

Blanshard et al., "Gastric secretion of parathyroid function in rats," *AJP*, 196(4):844-846, 1959.

Filip et al., "Design, implementation, and testing of a miniature self-stabilizing capsule endoscope with wireless image transmission capabilities," *International Journal "Information Technologies & Knowledge"*, 5(1):3-24, 2011.

Filip et al., "Progress in self-stabilizing capsules for imaging of the large intestine," *ICECS*, pp. 231-234, 2010.

Givel et al, "2.3 Generation and control of colorectal motility," in *Anorectal and Colonic Diseases: A Practical Guide to Their Management*, $3^{rd}$ Ed., S. Laurberg and K. Krogh, Ed., New York: Springer, 2010, pp. 20-21.

Graebel, "Stability of submerged and floating bodies," in *Engineering fluid mechanics*, Ed. New York: Taylor and Smith, 2001, pp. 73-74.

Happel & Brenner, "The behaviour of fluids in slow motion," in *Low Reynolds Number Hydrodynamics: With Special Applications to Particulate Media*, Ed. Boston: Kluwer, 1983, pp. 23-58.

Jin & Xu, "Numerical Study of the Unsteady Aerodynamics of Freely Falling Plates", *Communication in Computational Physics*, 3(4):834-851, 2008.

Joseph & Liu, "Orientation of long bodies falling in a viscoelastic liquid", *J. Rheol.*, 37: 961-983, 1993.

Kim et al., "Motion dynamics of three-dimensional bodies falling through water", Proc. 17-th IWWWFB (ed. By R.C.T. Rainey & S.F. Lee), pp. 81-84, 2002.

Liao et al., "Indications and detection, completion, and retention rates of small bowel capsule endoscopy: a systematic review", *Gastrointest Endosc*, 71(2):280-286, 2010.

Marghitu, "Buoyancy and flotation," in *Mechanical engineer's handbook*, Ed. San Diego: Academic press, 2001, pp. 565-566.

United States Navy, B. Buoyancy, in *The Submarine: Basic Enlisted Submarine Text*, Ed. Washington: United States government printing office, 2967, pp. 18-23.

Wang et al., "Sedimentation of Cylindrical Particles in a Viscoelastic Liquid: Shape-Tilting", *China Particuology*, 2(1):13-18, 2004.

Becker, "The Effects of Shape and Reynolds Number on Drag in the Motion of a Freely Oriented Body in an Infinite Fluid," *Can. J. Chem. Eng.*, 37:85-91, 1959.

\* cited by examiner

SELF-STABILIZED ENCAPSULATED IMAGING SYSTEM

CROSS-REFERENCE TO RELATED APPLICATIONS

This application claims the benefit under 35 USC 119(e) of U.S. provisional patent application No. 60/650,278 filed Feb. 4, 2005.

FIELD OF THE INVENTION

The present invention relates generally to imaging of the gastrointestinal organs and, more particularly, to the imaging of gastrointestinal organs using a self-orienting, capsule-based imaging system.

BACKGROUND OF THE INVENTION

Recent advances in low-power complementary metal-oxide silicon (CMOS) imagers, mixed signal application specific integrated circuit (ASIC) and white light emitting diodes (LEDs) has led to a swallowable video capsule for endoscopy [See, e.g., Arkady Clukhovsky, "Wireless Capsule Endoscopy", Sensor Review, 23, no. 2, pp. 128-133 (2003).]. Capsule-based imaging of gastrointestinal organs was introduced in 1997 [See, e.g., Iddan et al., "In Vivo Video Camera System", U.S. Pat. No. 5,604,531, Feb. 18, 1997.], and has since become a preferred imaging modality for the small intestine due to its non-invasiveness and its capability for wirelessly delivering video imaging information [See, e.g., Roberto de Franchis et al., "Small Bowel Malignancy," Gastrointest. Endoscopy Clin. N. Am., Vol. 14, pp. 139-148 (2004); and Doron Fischer et al., "Capsule endoscopy: the localization system", Gastrointest. Endoscopy Clin. N. Am., 14, pp. 25-31 (2004).] The wireless capsule endoscope presently sold by Given® Engineering LTD, Yoqneam, Israel as the M2A™ Swallowable Imaging Capsule, is 11 mm by 26 mm, pill-shaped, and contains 4 longitudinally positioned light emitting diodes (LEDs), a longitudinally disposed CMOS imager, lenses, a battery and an antenna/transmitter.

Application of this technology to other gastrointestinal organs, including the esophagus, the stomach, the duodenum, and the colon exposes the difficulty that, for organs having significantly larger lumens than the small intestine, the average diameter of which is about 2.5 cm, the imaging capsule may tumble during its passage through a larger-lumen organ since the capsule lacks a mechanism for laterally stabilizing itself, thereby precluding meaningful interpretation of the acquired images.

Accordingly, it is an object of the present invention to provide an apparatus and method for facilitating capsule-based imaging of the gastrointestinal tract.

Another object of the invention is to provide an apparatus and method for imaging the larger-lumen gastrointestinal organs from which meaningful images may be generated.

Additional objects, advantages and novel features of the invention will be set forth, in part, in the description that follows, and, in part, will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, there is provided according to an aspect of the invention an apparatus for imaging walls of a gastrointestinal organ, the apparatus comprising a swallowable capsule, an imaging system carried by the capsule, an expandable material attached to the capsule by a controllable releasing mechanism; and the expandable material being expandable to stabilize the capsule in the gastrointestinal organ. In other aspects of the apparatus, the capsule has a cylindrical portion. According to another aspect of the invention, the capsule has a first end and a second end; a first expandable material attached to the first end of the capsule; a second expandable material attached to the second end of the capsule; an outer component for sealing the capsule, the first expandable material and the second expandable material, and adapted to dissolve or break within a targeted gastrointestinal organ, but not in other gastrointestinal organs, thereby permitting swelling of the first expandable material and the second expandable material such that the capsule is laterally stabilized within the targeted gastrointestinal organ while being able to moved through the gastrointestinal organs by peristalsis and/or other means. In still further aspects of the invention there are provided as part of the imaging system at least one light emitting diode adapted for illuminating a portion of the interior of the targeted gastrointestinal organ; at least one imager for imaging the internal wall of the targeted gastrointestinal organ, and generating signals bearing the images of the internal wall; a wireless transmitter; and means for controlling the operation of the at least one light emitting diode and the at least one imager, for receiving the signals from the at least one imager, and for directing the signals to the wireless transmitter for transmission out of the targeted gastrointestinal organ.

In another aspect of the invention, and in accordance with its objects and purposes, the apparatus for imaging gastrointestinal organs may include a combination of: a transparent cylindrical capsule having a first end and a second end; a first expandable material attached to the first end of the capsule; a second expandable material attached to the second end of the capsule; means for sealing the capsule, the first expandable material and the second expandable material, and adapted to dissolve or break within a targeted gastrointestinal organ, but not in other gastrointestinal organs, thereby permitting swelling of the first expandable material and the second expandable material such that the capsule is laterally stabilized within the targeted gastrointestinal organ while being able to be moved through the gastrointestinal organs by peristalsis and/or other means; means for illuminating a portion of the interior of the targeted gastrointestinal organ; at least one imager for imaging the internal wall of the targeted gastrointestinal organ, and generating signals bearing the images of the internal wall; means for wirelessly transmitting the signals bearing images of the internal wall out of the targeted gastrointestinal organ; means for controlling the operation of the means for illuminating and the at least one imager, for receiving the signals from the at least one imager, and for directing the received signals to the means for wirelessly transmitting.

In still another aspect of the present invention, and in accordance with its objects and purposes, the method for imaging gastrointestinal organs hereof includes the steps of: introducing a capsule adapted for obtaining images of the internal walls of structures through which it passes and for wirelessly transmitting these images, into the gastrointestinal tract of a patient; moving the capsule through the gastrointestinal tract to an organ to be imaged; stabilizing the capsule in the organ of interest such that the capsule does not tumble; activating the imaging function of the capsule in the organ to be imaged; transmitting the images obtained by the capsule to an image processor external to the patient; and moving the capsule out of the gastrointestinal tract.

Benefits and advantages of the present invention include, but are not limited to, the ability to obtain accurate and interpretable images of the interior of a targeted gastrointestinal organ.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF PREFERRED EMBODIMENTS OF THE INVENTION

Briefly, the present invention includes an apparatus and method for imaging gastrointestinal organs from which meaningful images may be generated. The apparatus hereof comprises a wireless imaging capsule having an outer component that dissolves or breaks in the targeted organ, thereby permitting swelling of expandable materials disposed on each end of the capsule. As a result, the capsule is oriented and self-stabilizing against tumbling. At about the time of the expansion process, during this process or just afterwards, imaging components in the capsule are activated. These may include light emitting diodes (LEDs) for illuminating the interior of the organ of interest, and image sensors. The oriented and stabilized wireless capsule endoscope can then provide images from which details of the inner walls for organs having large lumens can be reconstructed. Although the colon has been chosen as an example of a large-lumen organ in the following description, application of the present invention is not limited to this organ.

Figure 1:
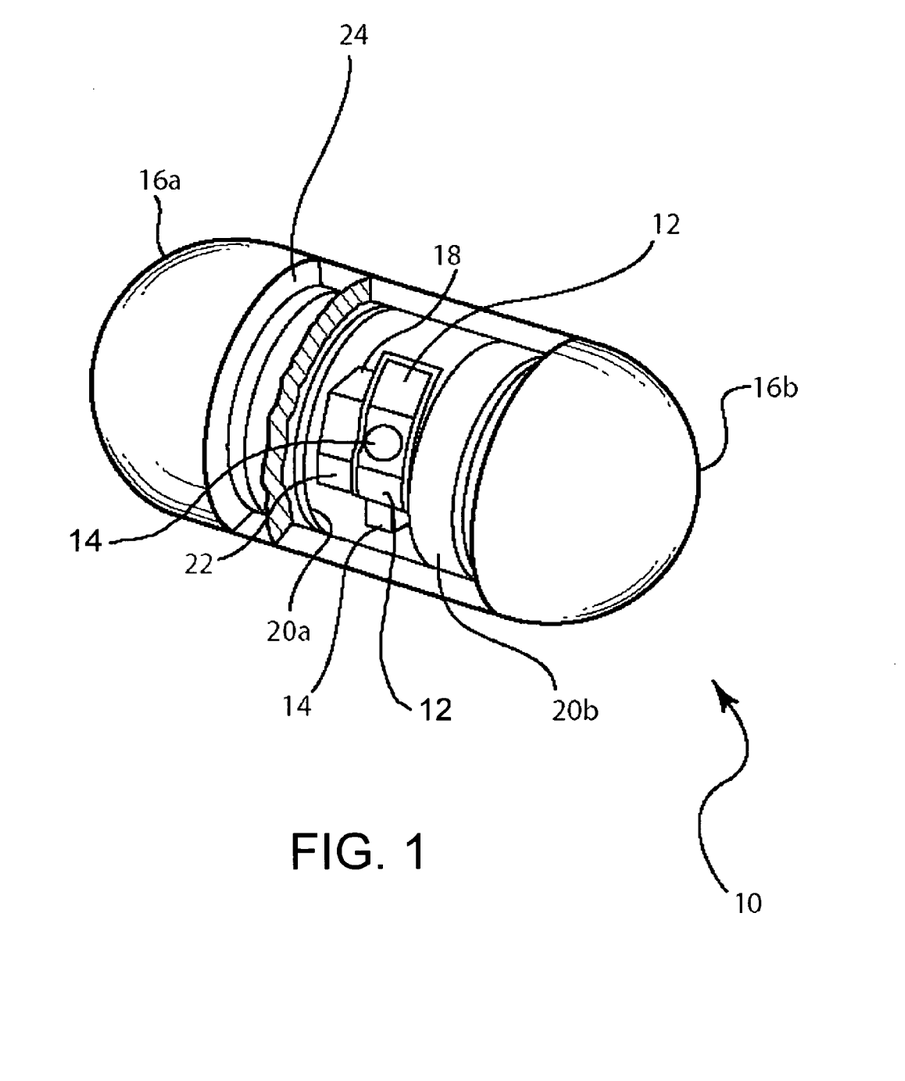
FIG. 1 is a schematic representation of an embodiment of the present wireless endoscope capsule showing, in particular, the casing, the interior components and the expandable material thereof.

Reference will now be made in detail to the present preferred embodiments of the invention examples of which are illustrated in the accompanying drawings. In what follows, identical callouts will be used for similar or identical structure. Turning now to FIG. 1 hereof, shown is a schematic representation of self-stabilizing capsules, 10, of the present apparatus which may include an outer protective coating or shell 11 (FIG. 5), which dissolves or breaks after capsule 10 enters the gastrointestinal organ to be imaged.

At least one imager, 12, and at least one white light emitting diode (LED), 14, circumferentially arranged on capsule 10 are then activated. It should be mentioned that complementary metal-oxide silicon (CMOS) imagers may be used in accordance with the teachings of the present invention. At about the same time that the protective coating or shell breaks or dissolves the expandable parts, 16a and 16b, of capsule 10 expand and stabilize the capsule in the lumen of the colon. The capsule is moved through the colon by peristalsis. At least one radio-frequency (RF) transmitter, 18, transmits the acquired images at an appropriate frame rate to an external receiver and data processor adapted for reproducing the received images, also not shown in FIG. 1. Batteries, 20a and 20b, furnish electrical power to the electronic components of capsule 10. Controller, 22, directs the functioning of the components of capsule 10, including directing transmitter 18 to communicate data collected by imagers 12 to an external receiver, not shown in FIG. 1. Capsule casing, 24, provides protection for the capsule components from gastrointestinal fluids and from mechanical destruction, and furnishes scaffolding from which the components can be effectively mounted and deployed. A system may also be used, such as a magnetic location system, for locating the capsule in the targeted gastrointestinal organ.

Having generally described the components of capsule 10, the following description provides greater detail thereof.

Outer Component: The outer component may include a capsule or a coating which remains intact throughout the capsule's movement through the GI tract until the colon, or other targeted gastrointestinal organ, has been reached. Capsules are preferred by patients since they are generally easy to swallow. Once within the colon, the outer component dissolves or breaks to allow the expandable component to enlarge and stabilize the capsule. The imaging components are activated after this occurs. The outer component may be fabricated from a colon-targeting material that would be stable in the stomach and small intestine, but would dissolve or break once in the colon. For imaging the small intestine, as another example, a small-intestine targeting material would be used. In U.S. Pat. No. 5,688,776 for "Crosslinked polysaccharides, process for their preparation and their use," which was issued to Bauer et al. on Nov. 18, 1997, certain crosslinked polysaccharides suitable for colon-targeting due to their enzymatic degradability by the microflora of the large intestine are described. It was also disclosed in Bauer et al. that using pH alone to select an organ would be insufficient to target the colon as opposed to the small intestine, since there is only a small difference in pH values between the small intestine and the large intestine. Crosslinked polysaccharides, by contrast, are stable in the small intestine since they are not attacked by amylases found in the small intestine. A useful colon-targeting material chosen for the present design would therefore be a crosslinked polysaccharide, an example of which is crosslinked dextran.

It has been found that crosslinked dextran capsules provide a better colon-specific drug release by limiting diffusional release in the upper GI tract. Such capsules also degrade more rapidly in the colon [See, e.g., H. Brondsted et al. "Crosslinked dextran-a new capsule material for colon targeting of drugs," Journal of controlled Release, 53, pp. 7-13 (1998)], when compared to matrix systems. It was further found that dextran capsules quickly break and release drugs as a dose dump in experiments simulating the arrival of the capsule in the colon [See, e.g. Brondsted et al., supra].

Imaging Components: Imaging components include: (a) a casing; (b) imagers; (c) LEDs; (d) at least one radiofrequency (RF) transmitter; (e) at least one battery; and (f) a control unit. Casing: The casing may be made of a transparent, inert material through which light from the LEDs can illuminate the organ features such that these features can be identified by the imagers. The material should also have sufficient structural strength so as not to break in the gastrointestinal environment. Polymeric materials including polycarbonates, and polyetherimide [See, e.g., Long, "Self-propelled, intraluminal device with electrode configuration and method of use," U.S. Patent application No. 0125788A, filed on Jul. 3, 2003.] are known by those skilled in the art to have these properties. A generally cylindrical shape for the casing enabled the prediction of the increase in volume of the expandable material.

Imagers: At least one imager (there may be X imagers, where X≥1) disposed in the capsule, captures images of the walls of the colon at a particular position in the snapshot mode. All of the imagers take pictures of the interior of the colonic wall at same position along the length of the colon, but of different portions of the wall within a particular colonic wall band, before being moved to another position by peristalsis. For example, three such imagers may be circumferentially positioned, each providing an imaging angle of ≥120° when associated with appropriate optical lenses, thereby providing 360° imaging of a band of the colonic wall. With a larger number of imagers, the overlap of the captured images will be greater, and the composite images of each colonic band should be improved. However, since the capsule should be able to be swallowed by a patient, and should be able to reach the colon, the dimensions of the capsule casing are constrained. Therefore, the number of imagers is limited due to space constraints.

It is known that the propagation velocity differs in various sections of the colon. The time resolution of the sampling of the imagers is chosen to ensure that meaningful data are collected; that is, the minimum number of frames required for a particular distance traveled depends on the speed of the capsule in the location of the fastest velocity in the colon. The imagers may be directed by a controller to record images with a desired time resolution. The time resolution of the sampling of the imagers defines the power needed per frame, which in turn determines the number of imagers that can be used for a certain amount of power supplied. Dynamic time resolution for image sampling may be achieved if a three-axis accelerometer, such as an Analog Devices, Inc., ADXL330, accelerometer, as an example, is integrated into the capsule, so that the velocity of propagation is monitored and the time intervals between successive image snapshots are adjusted accordingly.

As will be described hereinbelow, 3 LEDs may be used; therefore based on geometrical considerations, 3 CMOS imagers may be used. It may also be shown that a useful maximum width for the imagers is about 9.5 mm. Snapshot CMOS imagers between ⅓ and ½ in. in size would fit inside the proposed capsule. Some commercially available snapshot imagers from Micron Technology Inc. of Boise Idaho have the dimensions 0.5×0.55 in. [See, e.g., Micron Technology Inc., CMOS Image Sensors, 2004]. For example, the Micron Technology imager MT9V 403 is a 0.3 mega-pixel, capable of 0-200 fps and requires 39.4 mA at 200 fps for a 3.3 V power supply. This imager may be used in accordance with the present invention. Lenses providing a sufficiently large imaging angle may be employed in conjunction with the imagers.

Light Emitting Diodes LEDs: The circumferentially disposed LEDs provide light for capturing images over a 360° range. Furthermore, due to space constraint in the approximately 11 mm diameter casing, the LEDs have to be small and yet provide enough luminous intensity for useful images to be obtained. It is desirable that luminous intensities should be sufficient for illumination in the region of the colon where the lumen is largest; that is, the cecum. The LEDs are synchronized with the imagers through a control system described below such that the images from the circumferentially arranged imagers can be simultaneously captured. The power required by the LEDs clearly depends on the number and type of LEDs used.

With the availability of 180°-viewing angle surface-mounted LEDs, two LEDs may be used to cover a 360° viewing range; however, the intensities of such LEDs are presently too low [See, e.g., Fairchild Semiconductor Corporation, 2001. (Online)]. Therefore, for the proposed apparatus, 3 surface-mounted LEDs having viewing angles of between about 120° and 140° degrees may be chosen. Light emitting diodes having these characteristics are available in small sizes, can be surface mounted, and can be disposed in an 11 mm diameter capsule [See, e.g., Fairchild Semiconductor Corporation, supra.]. Light emitting diodes suitable for use in the present invention may also have frequencies and duty cycles that match the time resolution and image transfer rates of the image sensors.

Figure 2:
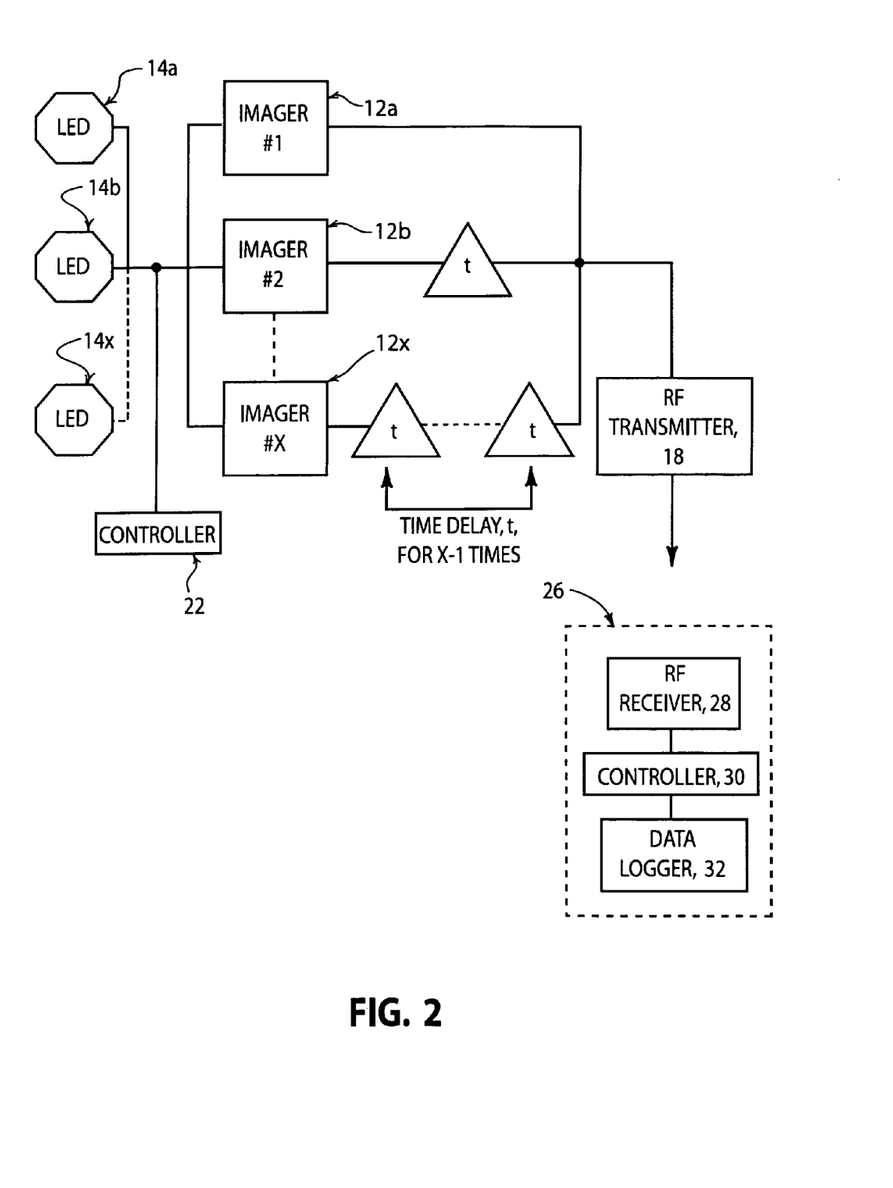
FIG. 2 is a schematic representation of an embodiment of the apparatus for data collection hereof via a serial port, and transmission thereof from the RF transmitter in the capsule of FIG. 1 to a receiver outside of the patient.

Radiofrequency (RF) transmitter; At least one RF transmitter equipped with an appropriate antenna is used to wirelessly transmit data from the imagers to an external receiver, also equipped with an appropriate antenna. There may be the same number of RF transmitters (X≥1) to transmit the data as there are imagers or, if data from the imagers are time-multiplexed so that the data collected is serially directed to the RF transmitters, fewer transmitters can be used to save power and space. FIG. 2 is a schematic representation of one embodiment of data collection using a serial port. At least one RF transmitter 18 may be synchronized with the imagers 12a-12x and LEDs 14 through controller 22 that may be integrated into one application specific integrated circuit (ASIC) chip. Data collection from imagers 12 may be multiplexed serially by controller 22 to an RF transmitter. There will be a different delay in data transmission for each imager, in order to enable such serial multiplexing. For example, a first imager may transmit data when it is ready, a second imager may transmit its data after a delay having duration, t, where t is the time required by the first imager to transmit its data, a third imager may transmit data after 2 such delays, etc. The data collected is directed to RF transmitter 18 for transmission to data processor, 26, located external to the patent and including RF receiver, 28, from which received data is directed by controller, 30, to data logger, 32, for storage and readout.

Figure 3:
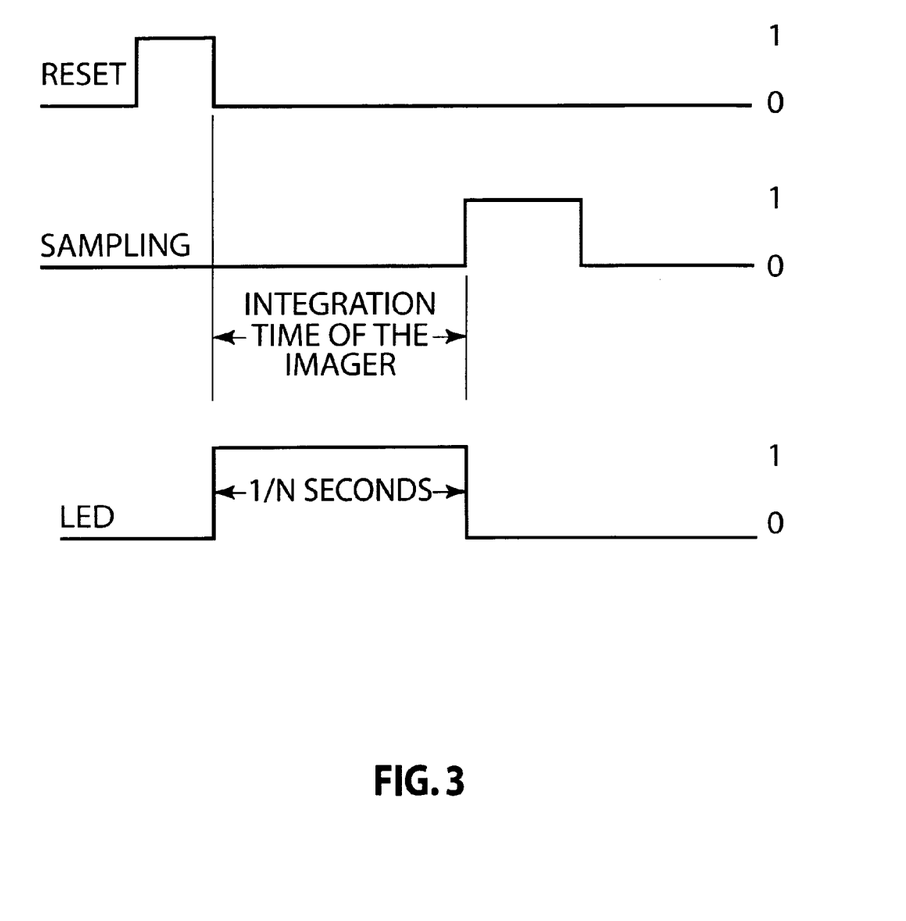
FIG. 3 shows an example of the timing diagram for an imager and a light emitting diode in a frame captured by the imager.

For the present design, the MAX1472 amplitude shift-keying (ASK) transmitter from Maxim Integrated Products, Inc. (Sunnyvale, Calif.) would be useful. It is a phase-locked-loop (PLL) transmitter which operates in the 300 MHz to 450 MHz frequency range. The transmitter has a current consumption of less than 9 mA and is in a 3 mm×3 mm SOT23 package. Assuming that the images are time-multiplexed in accordance with the teachings of the present invention, one transmitter may be chosen for the proposed design. An ASK superheterodyne receiver, MAX1473, may be used to receive the transmitted data direct to a data logger, as illustrated in FIG. 3.

Controller: The synchronization of the image sensors and LEDs can be achieved using a controller which can be a separate entity or integrated in one ASIC chip with the RF transmitter. Microcontrollers, field-programmable gate arrays (FPGAs) and digital signal processing (DSP) technologies can be used for this purpose.

The controller provides the signals for operating both the imagers and the LEDs based on a chosen sampling and data transfer rate. Additional processing may be required to make efficient use of the transfer rate of the image data. Since factors such as the propagation velocity through the colon and the total transit time in the colon vary among individuals, in the situation of an individual having a slow propagation velocity while the time resolution of the imager is being determined by the fastest possible velocity, the imager would sample unnecessarily with the capsule moving slowly. The power initially allocated for a particular sampling rate might not then be sufficient for the entire travel of the capsule in the colon.

The difference in propagating velocities for each individual may be accommodated by introducing a control system having a feedback loop so that the sampling rates of the imagers are adjusted according to the actual propagating velocity of the capsule. This method uses the power efficiently and is not directly dependent on the propagating velocity, but on the length of the colon. That is, sampling may be performed over the length of travel, rather than at a uniform sampling resolution, making the design more adaptable to any individual.

Batteries: Power supplied by the batteries may determine the number of imagers and LEDs that can be used, since it is desirable to image the entire colon. Based on the average transit time, the amount of time, T, which the batteries should operate can be chosen. The fastest propagating velocity in the colon, V, and the time resolution of the sampling process, defines a sampling distance, R, at which views of the colon segments are obtained. The total number of frames, D, can then be calculated from the equation D=V·T/R. For Z (Z≥1) batteries, the power consumption per frame of one imager, Y (Y>0), can be calculated. The total power consumption for Z batteries for X (X≥1) imagers for a single frame is X·Y. Therefore, values for X, Z and R can readily be selected. To minimize the power required by the LEDs, these devices can be pulsed for 1/N s in synchronization with a chosen frame rate of the imagers (1/N s), where N is the maximum image transfer rate in frames per second (fps). This means that during 1-1/N s, the LEDs will be on stand-by. The power consumption of the LEDs then depends on the maximum current at a particular frequency and duty factor, and the stand-by current requirements thereof. FIG. 3 shows a timing diagram for an imager and an LED, wherein LED power consumption may be minimized. The LEDs operate during the same period that the imagers are collecting data, after which time period both the LEDs and the imagers are shut down.

Transcutaneous induction, as an example, may be useful for providing additional power. That is, the capsule would contain a coil in which a current could be induced by a changing magnetic field generated by a transmitter worn by the patient. Upon rectification, this current could be used to charge the batteries, whereby the battery may be discharged and charged with the consequence of improving the life of the battery.

As an example of current usage, estimating LEDs at 75 mA (for 3); imagers at 118.2 mA; and RF transmitters at 9.1 mA, one obtains a total of 192.3 mA without including the controller and multiplexer. These values were quoted from commercially available products: for MT9V 403, as an example, with the imagers and the RF transmitter assumed to be operating at the highest tolerable temperature, etc.

The batteries may be activated after the outer protective coating or shell of capsule 10 is dissolved in the colon by a switch or other mechanism (not shown in FIG. 1 hereof) adapted for such purpose. See, for example, U.S. Pat. No. 6,635,834 for "System and Method to Delay Closure of a Normally Closed Electrical Circuit" which issued to Justin Bernard Wenner on Oct. 21, 2003, for a description of a device for allowing an electrical circuit to close when a material holding the circuit open is exposed to an environment having a specific pH.

Expandable Components: Expandable material is disposed at each end of the shell in the embodiment shown, but may be provided at one end only. It provides stability to the imaging modality upon expansion. The properties of the expandable material should enable it to (1) expand extensively; (2) expand in a relatively short amount of time; (3) exert reasonable pressure on the walls of the lumen; (4) be biocompatible and (5) have a stable consistency.

Once the colon has been reached, the coating of the capsule dissolves and the expandable material starts to expand. The expansion thus starts in the cecum. The average diameter of the colon is about 6.5 cm [See, e.g., Thomas McCracken, *New Atlas of Human Anatomy*, New York, Barnes & Noble Books, (1999).]. For the expandable material to touch the walls of the colon upon expansion or at least have a similar capsule diameter to lumen diameter ratio for the small bowel capsule endoscopy (the diameter of the present capsule is 1.1 cm while that of the small bowel is 2.5 cm [See, e.g., McCracken, supra.]), 200-500% expansion is needed. This amount of self-expansion may be achieved using for example either of two mechanisms, as examples: (1) diffusion of water molecules by osmosis, which can be observed in hydro-gels, certain polymeric materials and mineral clays; and (2) release of potential energy resulting in an expansion of the material possessing the potential energy, which can be observed whenever a compressed or stretched material is released. Stents and springs are examples of this effect.

It should be mentioned that if a larger lumen organ is to be imaged, for example, the stomach, stabilization of the capsule would require a significant expansion of the expandable material, thereby preventing the stabilized capsule from passing into the duodenum. In U.S. Patent Application Publication No. US2004/0192582A1 for Ingestible Formulations For Transient, Noninvasive Reduction Of Gastric Volume, by Daniel R. Burnett and Peter G. Edelman, expandable materials are described that are effective for being trapped in the stomach, while slowly dissolving therein such that they eventually pass into the duodenum.

The more rapid the expansion, the more rapidly the imaging capsule may be stabilized in the colon, thus allowing quality imaging of the organ as soon as the capsule enters the colon. The rate of expansion in osmosis depends on numerous factors, including the structure of the material, the membrane and the concentration of the solution. By contrast, the release of potential energy is rapid.

The pressure exerted upon expansion on the walls of the colon should not damage this organ. The net pressure that the walls of the colon can bear, $P_{net}$, can be calculated using the following equation [See, e.g., Ferdinand P. Beer and E. Russell Johnston, Jr., *Mechanics of Materials* (England: McGraw-Hill Book Co., Metric Edition, 1992).], assuming that the pressure applied on the walls would only result in a hoop stress and no longitudinal stress:

$$P_{net} = \sigma_T \frac{t}{R}, \text{ and } P_{s\cdot max} = \sigma_T \frac{t}{R} + P_{peristalsis},$$

where $P_{net}$ is the net pressure that the walls of the colon can bear upon expansion; $P_{s\ max}$ is the maximum swelling/expanding pressure on the walls of the colon upon expansion; $\sigma_T$ is the tensile strength of the colon; t is the thickness of the colonic walls; R is the inner radius of the colon; and $P_{peristalsis}$ is the peristaltic pressure in the colon. It should be noted that the net pressure applied on the walls of the colon is the difference between the maximum swelling/expanding pressure applied by the expandable material, $P_{s\,max}$ and the pressure exerted by the colonic walls on the device, peristalsis as shown in the equation for $P_{net}$ above. The difference between the maximum swelling/expanding pressure, $P_{s\,max}$ and the peristalsis pressure, $P_{peristalsis}$, should be less than the net pressure, $P_{net}$ so that no harm is caused to the colonic walls.

The expandable material should not being toxic and not cause inflammation or immunological ejection. The expandable material should not be permanently deformed by the peristaltic pressure. It should be able to deform under pressure but regain its original shape when the pressure is removed. The expanded material should also keep its consistency and not change state under the influence of water or colonic fluids.

Materials having desired properties were categorized according to their mechanism of expansion: osmosis, or the release of potential energy. The latter mechanism has proven to b effective in several medical applications such as stents that help relieve pathological obstruction of tubular structures in vascular, urologic and gastroenterological systems and self-expanding prostheses [See, e.g., Lauto et al. "Self-expandable chitosan stent: design and preparation", *Biomaterials*, 22, pp. 1869-1874 (2001).]. The concern with this mechanism is the shape and structure of the expanded material. Stents and other prostheses are mostly hollow at the center and the smooth traveling of the device by natural peristalsis in the GI tract is not guaranteed. The availability of stent structures that can resist the peristaltic motion in the colon without themselves moving makes osmosis the preferred mechanism for the proposed apparatus [See, e.g., "Medical stents for body lumens exhibiting peristaltic motion", U.S. Pat. No. 6,505,654, which issued to Andersen et al. on Jan. 14, 2003.].

Figure 4:
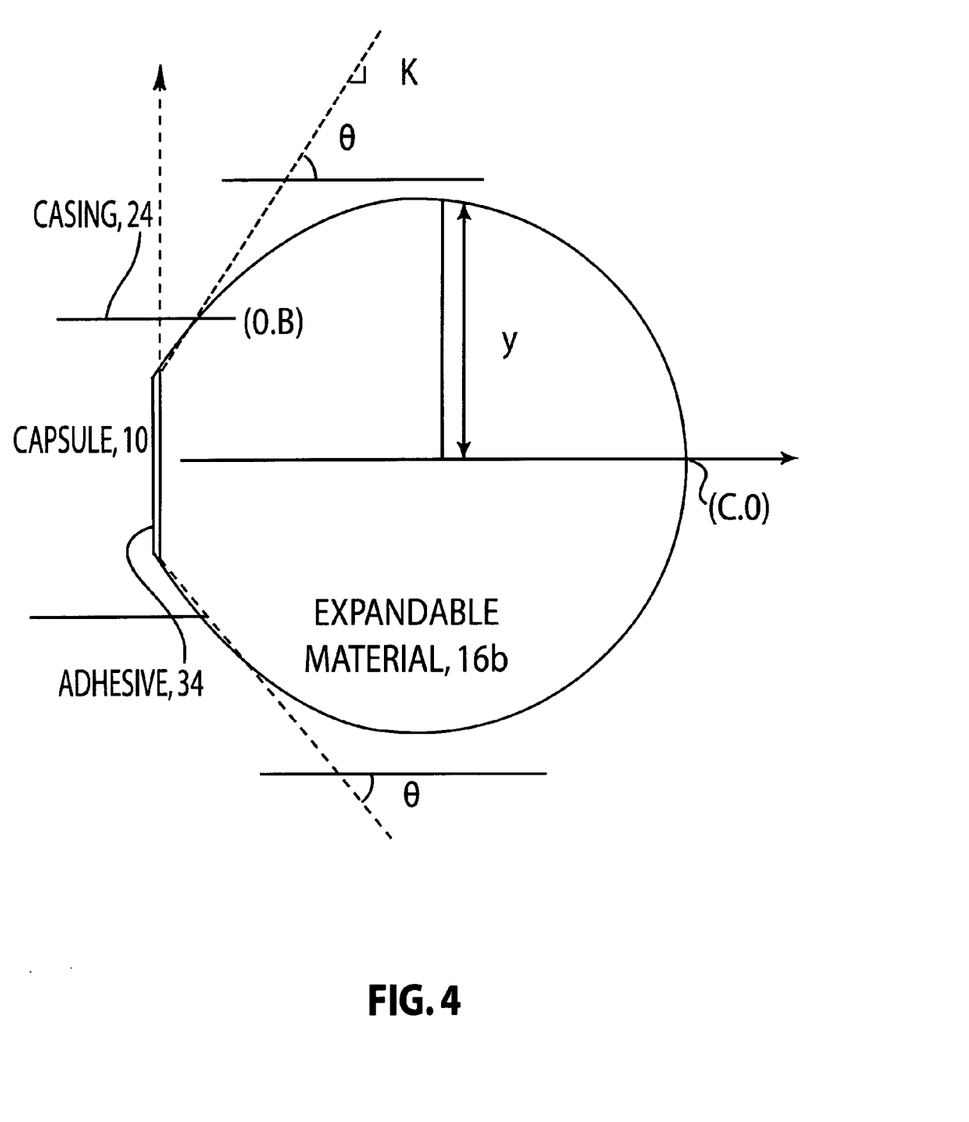
FIG. 4 is a schematic representation of the ends of the casing shown in FIG. 1 hereof, illustrating the expandable material.

The expandable material and the casing onto which it is attached is chosen to enable the prediction of the expanded volume, as well as to ensure that the expandable and imaging components do not become separated as a result of shearing. FIG. 4 shows expandable material 16b attached to one end of cylindrical capsule 10 illustrated in FIG. 1 hereof. Expandable material 16b is shown in its expanded state, and held in place by adhesive material, 34, which will be described in more detail hereinbelow. From the parameters identified in FIG. 4, the volume of the expandable material can be predicted by the following equation:

$$V = \left(\frac{-KC+B}{C^2}\right)^2 \frac{C^5}{5} + K^2 \frac{C^3}{3} + B^2 C +$$
$$2\left(\frac{-KC+B}{C^2}\right)C^4\left(\frac{K}{4}\right) + 2\left(\frac{-KC+B}{C^2}\right)\frac{C^3}{3}B + 2K\frac{C^2}{2}B$$

where K is the slope of the inclination of the casing or expandable component; C is the coordinate of the expanded material that crosses the horizontal axis; B is the coordinate of the expanded material that crosses the vertical axis; and V is the volume of the expanded material.

Bentonite is composed of smectite clay minerals which have properties which are related to their chemical composition, atomic structure, and morphology [See, e.g., R. E. Grim and N. Guven, "Properties and Uses of Bentonite", in *Bentonites: Geology, mineralogy, properties and uses*, Elsevier Scientific Publishing Company Amsterdam, pp. 217-248 (1978).]. The most important characteristic of bentonite is its potential to swell under the effect of a solvent, for example, water, due to the packet structure of the stratified bentonite See, e.g., Wieczorek et al., "Comparative Characteristics of Local an Foreign Bentonites", *Macromol. Symp.* 194, pp. 345-350 (2003).]. Other properties of bentonite include: (1) biocompatibility; (2) extensive swelling; (3) rapid swelling; (4) ability to exert a reasonable swelling pressure on the walls of the lumen; and (5) ability to withstand the pressure in the colon while remaining attached to the imaging component and keeping its consistency.

Natural minerals such as montmorillonite have been utilized as enterosorbents for withdrawing toxic and pathogenic components from the body of warm-blooded animals and humans. Acceptable daily doses of this natural mineral range between about 0.1 and 1.0 g per kg of body weight. U.S. Pat. No. 6,287,576 B1 for "Biostimulating Agent", which issued to Bgatov et al. on Sep. 11, 2001, describes a biostimulating agent that comprised of natural minerals containing not less than 2 weight (wt) % of montmorillonite. Therefore, the bentonite to be used for the proposed apparatus may contain greater than 92 wt % of montmorillonite in order to ensure its biocompatibility.

Bentonite contains montmorillonite, feldspar, quartz, etc., and the swelling of bentonite is caused by the swelling of the montmorillonite which is a swelling clay mineral. The montmorillonite mineral is a 2:1 layer consisting of an octahedral sheet sandwiched between two silica sheets as explained by Hideo Komine, in "Simplified evaluation for swelling characteristics of bentonites", *Engineering Geology*, 71, pp. 265-279 (2004). Interlayer water and exchangeable cations exist between the montmorillonite layers. Water is absorbed into the interlayers, resulting in expansion. The swelling pressure and swelling deformation of bentonite containing montmorillonite minerals are thus considered to be caused by the repulsive forces that occur between the layers. So, the swelling characteristics of bentonite can be evaluated by observing the swelling behavior of montmorillonite in bentonite [See, e.g., Wieczorek et al., supra].

The swelling characteristics of bentonite are characterized by the swelling pressure and swelling deformation. Komine (2004), supra, proposed a simplified method for evaluating the swelling characteristics of bentonite. The parameter "swelling volumetric strain of montmorillonite", $\epsilon^*_{sv}$, was earlier introduced by Komine and Ogata [See, H. Komine, and N. Ogata "Experimental study on swelling characteristics of sand-bentonite mixture for nuclear waste disposal", *Soils and Foundations*, 39, no. 2, pp. 83-97 (1999)] to synthetically evaluate the swelling characteristics of bentonites ($\epsilon^*_{sv}$ is the percentage volume increase of swelling deformation of montmorillonite when dry.). Komine (2004), supra, used equations derived by Komine and Ogata (1999), supra, to propose the simplified method.

It was found that the swelling characteristics of bentonites are strongly dependent on both the kinds of bentonites and the dry density. According to Komine (2004), supra, using the above-mentioned equations with the parameters derived from the type of bentonite used and its dry density, the swelling volumetric strain $\epsilon^*_{sv}$ (%), can be calculated from:

$$\varepsilon^*_{sv} = \frac{V_v + V_{sw}}{V_m} \times 100(\%),$$

where $V_v$ is the volume of voids in the composite material; $V_{sw}$ is the maximum swelling deformation of the composite material at constant vertical pressure ($V_{sw} \geq 0$); and $V_m$ is the volume of montmorillonite in the composite material.

From the experiments described by Komine (2004), the relationships between maximum swelling pressure and $\epsilon^*_{sv}$ and applied vertical pressure, and $\epsilon^*_{sv}$ can be obtained. Additionally, it should be noted that if the vertical pressure is greater than 200 KPa, the relationships between $\sigma_v$ and $\epsilon^*_{sv}$ are almost the same for all kinds of bentonite. From these graphs, and using the calculated value $\epsilon^*_{sv}$, the maximum swelling pressure and maximum swelling strain can be obtained. Evaluating flow and swelling characteristics of buffer and backfill materials may also be found in Komine (2004), supra.

Typical curves of swelling strain versus time at chosen bentonite contents have a hyperbolic shape [See, e.g., Komine 2004, supra]. It may be observed that a maximum swelling strain, $\epsilon_{s\ max}$, value, where $$\varepsilon_{smax} = \frac{V_{sw}}{V_v + V_{solid}} \times 100(\%),$$

and $V_{sw}$ and $V_v$ are defined hereinabove, and $V_{solid}$ is the volume of the composite material excluding voids, is reached after a period of time. The maximum swelling strain, $\epsilon_{s\ max}$, can be calculated from the asymptotic line of the hyperbola given by the equation:

$$\varepsilon_{smax} = \lim_{t \to \infty}\left(\frac{1}{\frac{a}{t}+b}\right) = \frac{1}{b}(\%).$$

It is known that the maximum swelling pressure depends on the initial dry density of the bentonite. It may also be noted that the time taken for this particular bentonite, Neokunibond (containing 76% montmorillonite), to reach maximum swelling pressure is less than 1000 min. Assuming that the slope before maximum swelling pressure is reached is linear, an equation relating swelling pressure and time can be obtained. The swelling pressure at a particular time can thus be obtained and the volumetric swelling strain, $\epsilon^*_{sv}$, found from a graph of maximum swelling pressure versus swelling volumetric strain.

Both the ionic concentration of pore water and the specific surface of bentonite are known to influence the swelling characteristics of soils [See, e.g., H. Komine and N. Ogata, "New equations for swelling characteristics of bentonite-based buffer materials" Canadian Geotechnical Journal, 40, pp. 460-475 (2003).]. In this reference, the authors proposed new equations for evaluating the swelling characteristics of bentonite-based buffer material by considering the influences of sand-bentonite mass ratio and the exchangeable-cation compositions in bentonite. It was also found that the swelling characteristics of the buffer material are significantly influenced by the chemical conditions of the bentonite and the surroundings [Komine and Ogata (2003), supra]. Komine (2004), supra, however found that the maximum swelling pressure is strongly influenced by the montmorillonite content rather than the exchangeable-cation compositions in bentonite. The effects of ions on the swelling characteristics can thus be ignored and the method proposed by Komine (2004), supra, used.

To prevent clogging of the expanded material in the colon, a maximum expansion of about 300% is needed to ensure that the expanded material's diameter does not exceed the smallest diameter of the colon. Using bentonite containing greater than 92 wt % of montmorillonite with different dry densities, the experiments described by Komine (2004), supra, can be performed to obtain graphs of swelling pressure versus time and maximum swelling pressure versus swelling volumetric strain. According to these graphs, depending on the swelling volumetric strain (and hence, on the volume expanded), a bentonite with a particular dry density is chosen such that the desired expanded volume can be achieved, and the maximum swelling pressure of bentonite reached in a minimum amount of time. The maximum swelling pressure should also be less than the net pressure that the colonic walls can bear. In order to achieve the purposes of the present invention, the bentonite should be firmly attached to the capsule bearing the imagers and associated microelectronic components; therefore, the bentonite may be mixed with appropriate biocompatible polymers in effective amounts to achieve the required bonding strength [See, e.g. U.S. Pat. No. 6,153,222 for "Volume-Expandable, Sheet-Like Application Form Suitable As An Active Substance Carrier, In Particular For Oral Application," which issued to Frank Becher on Nov. 28, 2000]. Expandable biocompatible polymers may also be used in the absence of bentonite. For example, microcrystalline hydrogels and polyolefins may be used. Carboxymethyl cellulose may also be used.

Adhesive Components: The adhesive material ensures that the expandable part remains attached to the imaging component throughout the capsule's travel in the GI tract, especially the colon. Due to the geometry of the capsule and pressure applied in the colon, there is a risk of the two components detaching from each other. The breaking strength should thus be greater than the maximum pressure applied in the colon which would arise if the peristaltic pressure holds one end of the expandable material fixed while random pulling pressure is applied on the remainder of the capsule. The random pressure is assumed to have a pulling effect; that is, a lateral pressure of the same magnitude as the transversally applied random pressure. The worst-case scenario would be where one end is fixed and the other is pulled laterally. It was found that the mean peak amplitude of antegrade propagating pressure waves for all colonic regions is significantly greater than that of the retrograde propagating pressure waves [See, e.g., Ian J. Cook et al., "Relationships between spatial patterns f colonic pressure and individual movements of content", Am. J. Physiol. Gastrointest. Liver Physiol., 278: G329-G341 (2000)]. The mean peak amplitude of antegrade propagating pressure waves is 41.8±2.3 mmHg; range 5-169 mmHg [See, e.g., Ian J. Cook et al., supra.]. A value of 300 mmHg (40 KP) is used to calculate the worst-case scenario for the present design.

The peristaltic pressure in the colon applied to various components of the capsule results in shearing that might cause the components to be detached from each other. The casing of the imaging component as been specially designed, not only to predict the expansion, but to make the expandable material fit more tightly in the casing upon expansion, thus preventing the expandable and imaging components from being detached as a result of shearing. Hence, in choosing an adhesive material, the shearing effect caused by the transversal peristaltic pressure can be disregarded.

The adhesive material should also be biocompatible. A cyanoacrylate adhesive was approved by the FDA in the U.S. in 1998 for Topical use to close skin incisions and lacerations [available from Protein Polymer Technologies Inc. of San Diego, Calif.]. Therefore, such adhesive is biocompatible. Moreover, cyanoacrylate adhesives set fast and have high strength. Several cyanoacrylate adhesives are available commercially having various breaking strengths. For the present apparatus, a cyanoacrylate adhesive manufactured by TOA-GOSEI Co., Ltd of Tokyo, Japan, named Aron Alpha 201, and having a breaking strength of 12.75 MPa may be chosen. This breaking strength is, therefore, greater than the maximum applied lateral pressure of 40 KPa. However, any suitable adhesive having the indicated properties may be used.

Figure 5:
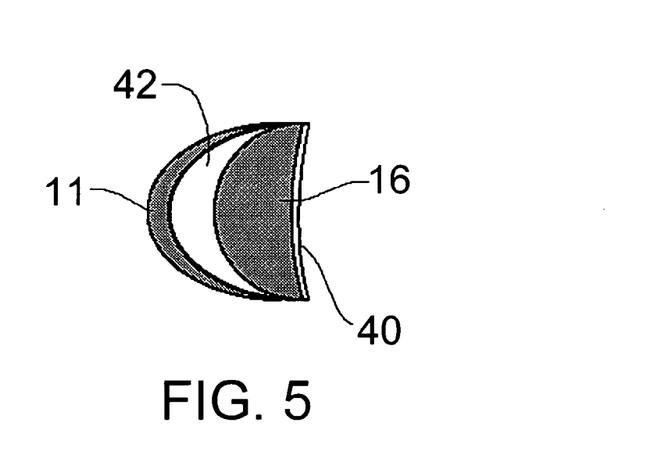
FIGS. 5 AND 6 are schematic representations of details of the expandable material.
Figure 6:
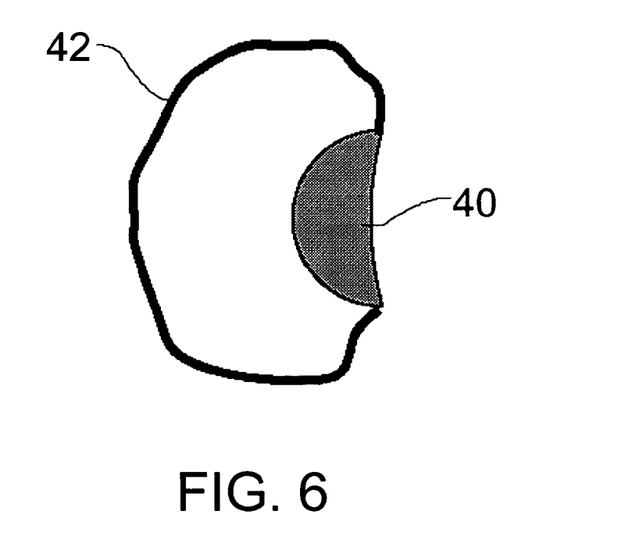

To avoid undesirable separation of parts of the expandable material from the main body of the expandable material, the expandable material may be encased in a liner. As shown in FIGS. 5 and 6, the liner is formed from an inner liner 40 and outer liner 42. The inner liner 40 is bonded to the capsule 10 with adhesive and remains in the same place during expansion of the expandable material 16. The outer liner 42 is folded about the outer periphery of the expandable material 16, as shown in FIG. 5, and expands as shown in FIG. 6 when the expandable material 16 is exposed to fluids of, for example, the colon, after dissolution or breaking of the coating 11. The outer liner 42 is sufficiently permeable to allow access of colon fluids to the expandable material 16, and may for example by made of spun bonded poly propylene or cotton. The inner liner 40 is preferably impermeable to fluids and may be made for example of a plastic film. The expandable component 16 may also include filler such as wood pulp. The coating 11 may extend all around the capsule 10 or may extend only as far around the capsule as required to secure the expandable material 16.

The foregoing description of the invention has been presented for purposes of illustration and description and is not intended to be exhaustive or to limit the invention to the precise form disclosed, and obviously many modifications and variations are possible in light of the above teaching.

The capsule is swallowable and thus should have smooth edges. The capsule may be any suitable shape such as cylindrical with domed ends, oblate, oval in cross-section, spherical, spherical-like, saucer, saucer-like, etc. The expandable material need only be placed on one side (as shown in FIG. 4), although an embodiment with the expandable material on both sides of the capsule has been described as an example. One or more imagers may be placed around the circumference of the capsule. If there is expandable material only on one side, one or more imagers may be longitudinally positioned at the opposite side of the capsule to the expandable material. If there is only one piece of expandable material, it may be largely spherical. It should be understood that references to spherical or cylindrical describe the approximate shape of the object. If the expandable material has a spherical shape when expanded, the expandable material will look more like a saucer when squeezed by the walls of the organ. The capsule wall may be entirely transparent, or a window or other sufficiently transparent portion may be provided in the capsule wall for the imager, preferably with appropriate lenses to ensure that an adequate image is collected by the imager. Preferably, the imager should not contact the walls of the organ. A person of average skill in the art may devise other methods for controlling the release of the expandable material based on the present disclosure. A particular method of controlling the release has been disclosed. It is possible also to store images collected by the imager on board the capsule for later retrieval.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto. In the claims, the word "comprising" is used in its inclusive sense and does not exclude other elements being present. The indefinite article "a" before a claim feature does not exclude more than one of the feature being present.

What is claimed is:

1. An apparatus for imaging walls of a gastrointestinal organ, the apparatus comprising:
    a swallowable capsule having a first end and a second end opposite the first end;
    an imaging system carried by the capsule;
    an expandable material attached to the first end of the capsule such that the second end of the capsule extends away from the expandable material, the expandable material contained by a controllable releasing mechanism, the expandable material comprising an absorbent material that is capable of swelling due to absorption of gastrointestinal fluid; and
    the expandable material being expandable to contact walls of the gastrointestinal organ and thereby stabilize the capsule against tumbling in the gastrointestinal organ.

2. The apparatus of claim 1 in which the capsule has a window for passage of light radiation into the imaging system.

3. The apparatus of claim 1 in which the controllable releasing mechanism comprises a component that releases the expandable material at a controlled location to expand.

4. The apparatus of claim 1 in which the controllable releasing mechanism comprises a material that at least partially dissolves due to action of an enzyme present in the small intestine or the colon.

5. The apparatus of claim 1 in which the controllable releasing mechanism comprises an outer component for sealing the capsule and the expandable material, and adapted to dissolve or break within the small intestine or colon, but not in the stomach, thereby permitting swelling of the expandable material such that the capsule is laterally stabilized within the small intestine or colon by contact with walls of the small intestine or colon while being able to move through the gastrointestinal tract.

6. The apparatus of claim 1 in which the imaging system comprises a light source and an imager.

7. The apparatus of claim 6 in which the imaging system further comprises a wireless transmitter for transmitting images of the walls of the gastrointestinal organ to a receiver.

8. The apparatus of claim 6 in which the light source is a light emitting diode adapted for illuminating a portion of the walls of the gastrointestinal organ.

9. The apparatus of claim 6 further comprising a controller configured for controlling the operation of the light source and imager.

10. The apparatus of claim 7 in which the imaging system comprises a plurality of light sources and imagers arranged circumferentially around the capsule.

11. The apparatus of claim 10 further comprising a controller configured for controlling the operation of the light source, imager and wireless transmitter.

12. An apparatus for imaging gastrointestinal organs, the apparatus comprising:
    a swallowable capsule;
    an expandable material attached to the capsule, the expandable material comprising an absorbent material that is capable of swelling due to absorption of gastrointestinal fluid;
    an outer component sealing the expandable material, the outer component adapted to dissolve or break within the small intestine or colon, but not in the stomach, thereby permitting swelling of the expandable material such that the capsule is laterally stabilized within the small intestine or colon by contact with walls of the small intestine or colon while being able to move through the gastrointestinal tract;

at least one light emitting diode adapted for illuminating a portion of the interior of the small intestine or colon;

at least one imager for imaging the internal wall of the small intestine or colon, and generating signals bearing the images of the internal wall;

a wireless transmitter in the capsule; and a controller operating the at least one light emitting diode and the at least one imager, for receiving the signals from the at least one imager, and for directing the signals to the wireless transmitter for transmission out of the small intestine or colon.

13. An apparatus for imaging gastrointestinal organs, the apparatus comprising:

a swallowable capsule;

an expandable material attached to the capsule, the expandable material comprising an absorbent material that is capable of swelling due to absorption of gastrointestinal fluid;

a sealing element sealing the expandable material, and adapted to dissolve or break within a targeted gastrointestinal organ thereby permitting swelling of the expandable material by absorption of gastrointestinal fluid such that the capsule is laterally stabilized within the targeted gastrointestinal organ by contact with walls of the targeted gastrointestinal organ while being able to be moved through the gastrointestinal organs;

an illuminator for illuminating a portion of the interior of the targeted gastrointestinal organ;

three or more imagers for imaging the internal wall of the targeted gastrointestinal organ, and generating signals bearing the images of the internal wall;

a wireless transmitter for transmitting the signals bearing images of the internal wall out of the targeted gastrointestinal organ; and a controller operating the illuminator and the three or more imagers, for receiving the signals from the three or more imagers, and for directing the received signals to the wireless transmitter.

14. A method for imaging gastrointestinal organs, the method comprising the steps of:
   (a) introducing a capsule according to claim 1 into the gastrointestinal tract of a patient; and
   (b) receiving images obtained by the capsule on an image processor external to the patient.

15. A method for imaging gastrointestinal organs, the method comprising the steps of:
   (a) introducing a capsule according to claim 12 into the gastrointestinal tract of a patient; and
   (b) receiving images obtained by the capsule on an image processor external to the patient.

16. A method for imaging gastrointestinal organs, the method comprising the steps of:
   (a) introducing a capsule according to claim 13 into the gastrointestinal tract of a patient; and
   (b) receiving images obtained by the capsule on an image processor external to the patient.

17. The apparatus of claim 12, where the outer component is adapted to dissolve or break within the colon, but not in the small intestine.

18. The apparatus of claim 12, where the outer component comprises a crosslinked polysaccharide or crosslinked dextran.

19. The apparatus of claim 12, where the outer component seals the capsule and the expandable material.

20. The apparatus of claim 13, where the sealing element seals the capsule and the expandable material.

21. The apparatus of claim 1, where the expandable material comprises a clay mineral.

22. The apparatus of claim 1, further comprising a permeable liner between the controlled releasing mechanism and the expandable material.

* * * * *